United States Patent
Pruss et al.

(10) Patent No.: US 9,320,745 B2
(45) Date of Patent: Apr. 26, 2016

(54) USE OF CHOLEST-4-EN-3-ONE DERIVATIVES FOR OBTAINING A CYTOPROTECTIVE DRUG

(75) Inventors: Rebecca Pruss, Cassis (FR); Bruno Buisson, Marseilles (FR); Thierry Bordet, Marseilles (FR)

(73) Assignee: TROPHOS, Marseilles (FR)

( * ) Notice: Subject to any disclaimer, the term of this patent is extended or adjusted under 35 U.S.C. 154(b) by 1012 days.

(21) Appl. No.: 12/295,269

(22) PCT Filed: Mar. 28, 2007

(86) PCT No.: PCT/FR2007/000530
§ 371 (c)(1),
(2), (4) Date: Mar. 5, 2009

(87) PCT Pub. No.: WO2007/118967
PCT Pub. Date: Oct. 25, 2007

(65) Prior Publication Data
US 2009/0186863 A1    Jul. 23, 2009

(30) Foreign Application Priority Data
Mar. 31, 2006  (FR) ...................................... 06 02799

(51) Int. Cl.
*A01N 45/00* (2006.01)
*A61K 31/56* (2006.01)
*A61K 31/575* (2006.01)

(52) U.S. Cl.
CPC .................................... *A61K 31/575* (2013.01)

(58) Field of Classification Search
CPC ...................................... A61K 31/575
USPC .................................... 514/169, 177
See application file for complete search history.

(56) References Cited

U.S. PATENT DOCUMENTS

2006/0217358 A1\*  9/2006  Bordet et al. ................. 514/177

FOREIGN PATENT DOCUMENTS

WO      WO 2004/082581      \*   9/2004

\* cited by examiner

*Primary Examiner* — Marcos Sznaidman
(74) *Attorney, Agent, or Firm* — Browdy and Neimark, PLLC

(57) ABSTRACT

The present invention relates to the use of cholest-4-en-3-one derivatives for obtaining a cytoprotective drug, with the exception of a neuroprotective drug.

3 Claims, No Drawings

USE OF CHOLEST-4-EN-3-ONE DERIVATIVES FOR OBTAINING A CYTOPROTECTIVE DRUG

The present invention relates to the use of cholest-4-en-3-one derivatives for obtaining a cytoprotective drug with the exception of a neuroprotective drug.

Cellular degenerative processes are characterized by dysfunction of cells often causing undesirable cell activities and cell death.

The cells have developed adaptation mechanisms in reaction to stress, which extend their lifetime or delay or prevent cell death (cytoprotective mechanisms).

However, these cytoprotective mechanisms are sometimes insufficient, inadequate or induced too late to be efficient and cells die. It may therefore prove to be of interest to have novel cytoprotective drugs, which would promote cytoprotection. This is one of the objects of the present invention.

The term <<cytoprotective>> makes reference to the capacity of either natural agents or not of protecting a cell against cell death, particularly pathological cell death, and/or against cell dysfunctions leading to cell death. These cell dysfunctions may for example be of mitochondrial origin such as a reduction in the capability of generating ATP, an incapability of capturing and/or retaining calcium, or the generation of free radicals.

Among the main mechanisms of cell death, a distinction is essentially made between necrosis, apoptosis, and necroptosis.

Necrosis is a so-called "accidental" cell death which occurs during damage to tissue. It is the plasmic membrane of the cell which is affected the most, causing modification of the homeostasis of the cell. The cells will soak up water to the extent that this will cause lysis of their plasmic membrane. This cell lysis leads to release of the cytoplasm contents into the surrounding medium. Necrosis is at the origin of the inflammatory process.

Necrosis may affect a set of cells or a tissue while other neighboring portions remain alive. The resulting transformation is mortification of the cells or of the tissues.

In other words, necrosis is defined by morphological modifications which occur when a cell reaches the end of its life as a result of events such as a significant trauma such as interruption or reduction of the blood supply at an organ, hyperthermia (significant rise in temperature), intoxication by a chemical, a physical shock, etc. . . .

One of the most known necroses is that of the myocardium during infarction (interruption of the blood stream supply at the cardiac muscle) due to occlusion (obstruction) of a coronary artery.

Apoptosis is an integral part of the normal physiology of an organism. It is a highly regulated physiological form of cell death and it is required for the survival of multicellular organisms. Apoptosis is a process which plays a primordial role during embryogenesis.

Cells in apoptosis or apoptotic cells will isolate themselves from the other cells. Apoptosis usually involves individual cells in a tissue and does not cause inflammation. One of the characteristic morphological points of apoptosis is the significant condensation of both the nucleus and the cytoplasm which induces significant reduction in the cell volume. The nucleus then fragments, each fragment are surrounded by a dual envelope. Apoptotic bodies (cytoplasmic and nuclear elements) are then released and will be absorbed through phagocytosis by neighboring cells.

Apoptosis may be induced in different ways. For instance, radiation, the presence of a chemical or hormone, are stimuli which may induce a cascade of apoptotic events in the cell. Intracellular signals such as incomplete mitosis or DNA damage may also induce apoptosis.

Apoptosis also occurs after the action of a genotoxic agent or during a disease. Certain pathologies are characterized by abnormal apoptosis, causing the loss of certain cell populations, as for example hepatotoxicity, retinopathies, cardiotoxicity.

A distinction is therefore made between physiological apoptosis and pathological apoptosis. The invention is essentially focused on pathological apoptosis.

There exist other mechanisms of cell death, such as for example necroptosis, which has characteristics of necrosis and apoptosis. A cell which is dying by necroptosis has similar characteristics to those of a cell dying by necrosis, but the biochemical steps of this mechanism are more similar to those of apoptosis. This mechanism of cell death for example occurs in ischemia.

Accordingly, one of the objects of the present invention is also to make novel drugs available with which it may be possible to prevent and/or treat necrosis and/or pathological apoptosis and/or necroptosis (anti-necrotic and/or anti-apoptotic and/or anti-necroptotic drugs).

Cell degenerative processes may result inter alia from pathological situations grouped under the term of degenerative diseases or affections, traumas or of exposure to various factors.

These traumas and factors may for example include exposure to radiations (UV, gamma radiations), hypoxia or lack of oxygen, lack of nutrients, lack of growth factors, poisons, cell toxins, waste, environmental toxins, free radicals, reactive oxygens or even certain medical events and/or procedures such as for example surgical traumas including transplantations of cells, tissues and organs. Chemical or biological agents may also be mentioned, used as therapeutic agents within the context of medical treatments such as for example cytostatic agents or anti-inflammatory agents.

The object of the invention is not to treat extracellular causes of pathologies or degenerative processes which may result in cell death, but actually the consequences at the cell level of said pathological processes or of said pathologies and particularly to protect the cell against said consequences.

Among the most significant pathological situations characterized by a degenerative process, other than neurological or neurodegenerative disorders to which the present invention is not directed, the following are found:

diseases of the bones, joints, connective tissue and cartilage, such as osteoporosis, osteomyelitis, arthritises including for example osteoarthritis, rheumatoid arthritis and psoriatic arthritis, avascular necrosis, progressive fibrodysplasia ossificans, rickets, Cushing's syndrome;

muscular diseases such as muscular dystrophy, such as for example Duchenne's muscular dystrophy, myotonic dystrophies, myopathies and myasthenias;

diseases of the skin, such as dermatitis, eczema, psoriasis, aging or even alterations of scarring;

cardiovascular diseases such as cardiac and/or vascular ischemia, myocardium infarction, ischemic cardiopathy, chronic or acute congestive heart failure, cardiac dysrythmia, atrial fibrillation, ventricular fibrillation, paroxystic tachycardia, congestive heart failure, hypertrophic cardiopathy, anoxia, hypoxia, secondary effects due to therapies with anticancer agents;

circulatory diseases such as atherosclerosis, arterial scleroses and peripheral vascular diseases, cerebrovascular strokes, aneurisms;

haematological and vascular diseases such as: anemia, vascular amyloidosis, haemorrhages, drepanocytosis, red cell fragmentation syndrome, neutropenia, leukopenia, medullar aplasia, pantocytopenia, thrombocytopenia, haemophilia;

lung diseases including pneumonia, asthma; obstructive chronic diseases of the lungs such as for example chronic bronchitis and emphysema;

diseases of the gastro-intestinal tract, such as ulcers;

diseases of the liver such as for example hepatitis particularly hepatitis of viral origin or having as a causative agent, other infectious agents, alcoholic hepatitis, auto-immune hepatitis, fulminating hepatitis, certain hereditary metabolic disorders, Wilson's disease, cirrhoses, alcoholic liver disease (ALD), diseases of the liver due to toxins and to drugs; steatoses such as for example:

non-alcoholic steatohepatitis (NASH), or accompanying exogenous intoxication with alcohol, drugs, viral or toxic hepatitis, complications of surgical procedures, metabolic diseases (such as diabetes, glucose intolerance syndrome, obesity, hyperlipidemias, dysfunctions of the hypothalamo-hypophyseal axis, abetalipoproteinemia, galactosemias, glycogen diseases, Wilson's disease, Weber-Christian's disease, Refsum's syndrome, carnitine deficiency, hepatic complications of inflammatory diseases of the digestive tract, auto-immune hepatitis.

By means of action on the steatosis or action on hepatic apoptosis regardless of the cause, the compounds may have a preventive action on the development of hepatic fibrosis and on preventing the occurrence of cirrhoses.

pancreas diseases such as for example acute or chronic pancreatitis;

I metabolic diseases such as diabetes mellitus and insipid diabetes, thyroiditis;

diseases of the kidneys, such as for example acute renal disorders or glomerulonephritis;

severe intoxications by chemicals, toxins or drugs;

degenerative diseases associated with the Acquired Immune Deficiency Syndrome (AIDS);

disorders associated with aging such as the syndrome of accelerated aging;

dental disorders such as those resulting in degradation of tissues such as for example periodontitis;

ophthalmic diseases or disorders including diabetic retinopathies, glaucoma, ptosis, optical atrophy, chronic progressive external opthalmoplegia, macular degenerations, retinal degeneration, retinitis pigmentosa, retinal holes or tears, retinal detachment, retinal ischemia, acute retinopathies associated with trauma, inflammatory degenerations, post-surgical complications, medicinal retinopathies, cataract;

disorders of the audition tracts, such as otosclerosis and deafness induced by antibiotics;

diseases associated with mitochrondria (mitochondrial pathologies), such as Friedrich's ataxia, congenital muscular dystrophy with structural mitochondrial abnormality, certain myopathies (MELAS syndrome, MERFF syndrome, Pearson's syndrome), MIDD (mitochondrial diabetes and deafness) syndrome, Wolfram's syndrome, dystonia.

The invention is also interested in protecting cells, tissues and/or transplanted organs, whether before, during (removal, transport and/or re-implantation) or after a transplantation.

Pharmacologically active compounds are still sought for controlling the degenerative processes mentioned above.

The present invention meets this demand for cytoprotective compounds. Indeed, the Applicant has discovered that cholest-4-en-3-one derivatives, and notably the oxime of cholest-4-en-3-one, are provided with remarkable cytoprotective properties.

This is why the object of the present invention is the use of at least one compound fitting formula I

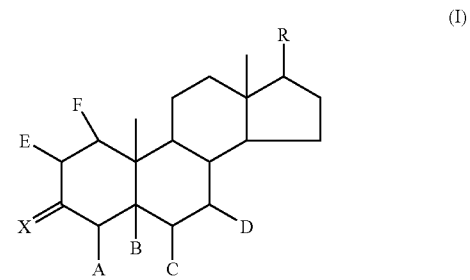

(I)

wherein X represents =N—OH group,
and R represents a group selected from

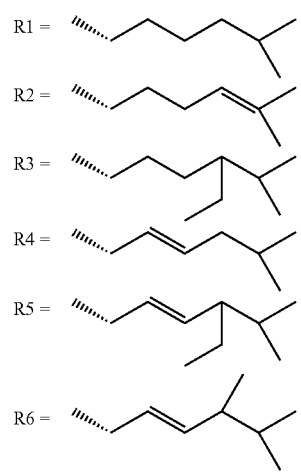

A represents a hydrogen atom or together with B a carbon-carbon bond,

B represents a hydrogen atom, a hydroxy group, or together with A a carbon-carbon bond, C represents a hydrogen atom or together with D a carbon-carbon bond, D represents a hydrogen atom or together with C a carbon-carbon bond, E represents a hydrogen atom or together with F a carbon-carbon bond, F represents a hydrogen atom or together with E a carbon-carbon bond, or one of its addition salts with pharmaceutically acceptable acids, or one of its esters or one of its addition salts with pharmaceutically acceptable acids of said esters, for preparing a cytoprotective drug, with the exception of a neuroprotective drug.

The compounds of formula I as defined above are known (WO2004/082581).

The addition salts with pharmaceutically acceptable acids may for example be salts formed with hydrochloric, hydrobromic, nitric, sulfuric, phosphoric, acetic, formic, propionic, benzoic, maleic, fumaric, succinic, tartaric, citric, oxalic, glyoxylic, aspartic, alkane-sulfonic acids such as methane- or ethane-sulfonic acids, arylsulfonic acids, such as benzene- or paratoluene-sulfonic acids or carboxylic acids.

According to the invention the oxime group represents pure or mixed syn and anti isomers, associated with the orientation of the N—O bond, relatively to the double bond C=N.

Among the compounds described above, the above compounds will be particularly retained, for which:

A represents together with B a carbon-carbon bond, C, D, represent a hydrogen atom, E, F represent a hydrogen atom or together a carbon-carbon bond and R has the meaning R1, A represents together with B a carbon-carbon bond, C, D, represent a hydrogen atom, E, F, represent a hydrogen atom and R has the meaning R2 or R3 or R4, A represents together with B a double bond, C represents together with D a carbon-carbon bond, E, F, represent a hydrogen atom, and R has the meaning R1 or R6, A represents together with B a double bond, C represents together with D a carbon-carbon bond, E represents together with F, a carbon-carbon bond, and R has the meaning R1, E represents together with F a double bond, C, D, A, B represent a hydrogen atom and R has the meaning R1, as well as their addition salts with pharmaceutically acceptable acids.

Advantageously, according to the invention, at least one compound of formula I is used, selected from
cholestan-3-one oxime,
cholest-4-en-3-one oxime,
cholest-1,4-dien-3-one oxime or one of its addition salts with pharmaceutically acceptable acids or one of its esters or one of its addition salts with pharmaceutically acceptable acids of said esters.

Preferentially, cholest-4-en-3-one oxime or cholest-1,4-dien-3-one oxime or one of its addition salts with pharmaceutically acceptable acids, or one of its esters or one of its addition salts with pharmaceutically acceptable acids of said esters, are used. The interesting cytoprotective properties of compounds of formula I justify their use for preparing a cytoprotective drug, particularly intended for treating or preventing necrosis, and/or pathological apoptosis, and/or necroptosis (anti-necrotic and/or anti-apoptotic and/or anti-necroptotic drugs) or further diseases such as diseases of the bones, joints, connective tissue and cartilage,
muscular diseases,
skin diseases,
cardiovascular diseases,
circulatory diseases,
haematological and vascular diseases,
diseases of the lung,
diseases of the gastrointestinal tract,
diseases of the liver,
diseases of the pancreas,
metabolic diseases,
diseases of the kidneys,
severe intoxications,
degenerative diseases associated with the Acquired Immune Deficiency Syndrome (AIDS),
disorders associated with aging,
dental disorders,
ophthalmic diseases or disorders,
diseases of the audition tracts,
diseases associated with mitochondria (mitochondrial pathologies).

The invention is also interested in protecting cells, tissues or transplanted organs, whether before, during (removal, transport and/or re-implantation) or after a transplantation.

Advantageously, the compounds of formula I may be used in preparing a drug intended for protecting cardiac cells (cardioprotective drug), protecting hepatic cells (hepatoprotective drug) or a drug intended for treating or preventing diseases associated with mitochondria.

According to the invention, the compound of formula I is advantageously present in the cytoprotective drug at physiologically effective doses; said drugs notably contain an effective cytoprotective dose of at least one of the compounds of formula I.

As drugs, the compounds fitting formula I, their esters, their addition salts with pharmaceutically acceptable acids as well as the addition salts with pharmaceutically acceptable acids of said esters may, be formulated for the digestive or parenteral route.

The drugs according to the invention may further comprise at least one other therapeutically active ingredient, whether it is active on the same pathology, or on a different pathology, for simultaneous, separate use or use spread out in time, notably when treating a subject affected by one of the pathologies mentioned earlier.

According to the invention, the compound of formula I may be used in the drug, mixed with one or more inert, i.e. pharmaceutically inactive and non-toxic, excipients or carriers. Mention may for example be made of saline, physiological, isotonic, buffered, solutions, etc., compatible with pharmaceutical use and known to one skilled in the art. The compositions may contain one or more agents or carriers selected from dispersants, solubilizers, stabilizers, preservatives, etc. Agents or carriers which may be used in formulations (liquid and/or injectable, and/or solid formulations) are notably methylcellulose, hydroxymethylcellulose, carboxymethyl cellulose, cyclodextrins, polysorbate 80, mannitol, gelatin, lactose, vegetable or animal oils, acacia, etc. Preferentially, vegetable oils are used. The compositions may be formulated as an injectable suspension, gels, oils, tablets, suppositories, powders, gelatin capsules, capsules, etc., possibly by means of galenic forms or devices providing prolonged and/or delayed release. For this type of formulation, an agent such as cellulose, carbonates or starches, is used advantageously.

Administration may be performed by any method known to one skilled in the art, preferably orally or by injection, typically via an intraperitoneal, intracerebral, intrathecal, intravenous, intra-arterial or intramuscular route. Oral administration is preferred. If this is a long term treatment, the preferred administration route will be sublingual, oral or transcutaneous.

For injections, the compounds are generally packaged as liquid suspensions, which may be injected by means of syringes or perfusions, for example. It is understood that the flow rate and/or the injected dose or generally the dose to be administered, may be adapted by one skilled in the art depending on the patient, on the pathology, on the administration method, etc. It is understood that repeated administrations may be performed, possibly in combination with other active ingredients or any pharmaceutically acceptable carrier (buffers, saline, isotonic solutions, in the presence of stabilizers, etc.).

The invention may be used in mammals, notably in humans.

Generally, the daily dose of the compound will be the minimum dose for obtaining the desired therapeutic effect. The dosages of the compounds described above and for example, of cholest-4-en-3-one oxime will generally be comprised between 0.001 to 100 mg per kilogram daily for humans.

If required, the daily dose may be administered in two, three, four, five, six or more takings per day or with multiple sub-doses administered at suitable intervals during the day.

The selected amount will depend on multiple factors, in particular on the administration route, on the administration duration, on the moment of administration, on the elimination rate of the compound, on the different product(s) used in combination with the compound, on the age, on the weight and on the physical condition of the patient, as well as on his/her medical history and on any other information known in medicine.

The prescription of the attending physician may begin with dosages less than those generally used, and these dosages will then be gradually increased in order to better control the occurrence of possible secondary effects.

EXAMPLE 1

Anti-Apoptotic Effect of cholest-4-en-3-one Oxime

Anti-apoptotic properties of cholest-4-en-3-one oxime were analyzed on cardiomyocytes, by a contractile dysfunction test induced by doxorubicin.

A stock solution of cholest-4-en-3-one oxime at a concentration of 10 mM in 100% DMSO was used. The final concentration in DMSO was the same for all the experimental points, independently of the molecular concentrations used. cholest-4-en-3-one oxime was tested at concentrations of 0.3, 1 and 3 µM, diluted in a solution of Tyrode (composition en mmol/L: NaCl 135, KCL 5.4, $NaH_2PO_4$ 0.33, $CaCl_2$ 1.2, $MgCl_2$ 1.0, Hepes 10; pH adjusted to 7.4 with NaOH).

Methods

Contractility and Apoptosis of Rabbit Ventricular Cardiomyocytes

A.1 Obtaining Isolated Cells of Rabbit Ventricular Cardiomyocytes

Isolated ventricular cells are obtained from New Zealand male rabbit hearts as described in A. d'Anglemont de Tassigny et al., Fund. Clin. Pharmacol., 18: pp. 531-38, 2004. Briefly, the rabbits (2.0-2.5 kg) are anaesthesized with a pentobarbital (50 mg/kg) solution and then receive heparin (200 IU/kg). The hearts are excised and immediately perfused, for 10-15 minutes by means of a Langendorff apparatus without recirculation with an oxygenated (calcium-free) tyrode isotonic solution (95%, 2-5% $CO_2$) (in mM: NaCl 135, KCl 5.4, $Na_2PO_4$ 0.33, $MgCl_2$ 1.0, HEPES 10, pH adjusted to 7.4 with 1N NaOH at 37° C., 280-300 mOsmol/kg$H_2O$). Next, all the hearts were perfused for 3 minutes in a "recirculation" mode with the same calcium-free Tyrode solution (coronary flow rate, 10-15 mL/min) added with 1 mg/mL of type II collagenase and 0.28 mg/mL of type XIV protease. Finally all the hearts are perfused in a mode without recirculation with the same solution of Tyrode supplemented with 0.3 mM $CaCl_2$ for 10 min. The left ventricle is removed and cut into small pieces; cell dissociation is achieved by mild mechanical stirring. Extracellular calcium is added by increments every 15 minutes, in order to reach a physiological concentration of 1.0 mM. The isolated myocytes are maintained in a medium without serum containing (in mM) NaCl 110, KCl 5.4, $Na_2PO_4$ 0.33, $NaHCO_3$ 25, Glucose 5, $MgCl_2$ 0.8, $CaCl_2$ 1, pH adjusted to 7.4, right up to 1 h30 before experimentation. All the cells are rod-like, have a pale crossed striation and do not have any vesicle at their surface under an optical microscope.

A.2 Marking with Annexin V

Marking phosphatidylserine with annexin V was used as a quantitative method for measuring apoptosis by using the MiniMacs cell isolation kit (Miltenyi Biotec, Bergisch, Gladbach, Germany). Briefly, the cells exposing phosphatidylserine are marked with annexin V microbeads magnetically, and then passed into a column placed in a magnetic field. The marked cells (which have magnetically marked phosphatidylserine) are retained in the column whereas the non-marked ones (necrotic cells and non-apoptotic cells) are not retained. The column is removed from the magnetic field; the magnetically retained cells exposing phosphatidylserine are eluted as a positive fraction and counted with a Mallassez cell counter. The percentage of apoptotic cells is then referred to the initial number of cells.

A.3 Measurement of Caspase-3 Activity

Caspase-3 activity is used as a quantitative method for measuring apoptosis. Briefly, the cells are lysed and the supernatant is used for caspase-3 activity measurement by using the AK-005 kit (Biomol Research Laboratories, Plymouth Meeting, Pa., USA). The fluorogenic substrate for measuring caspase-3 activity (DEVD) is marked with the fluorochrome, 7-amino-4-methyl coumarin (AMC) which produces yellow-green fluorescence detectable in UV light at 360/460 nm for 210 min. AMC is released from the substrate by cleavage by caspase-3, the expression of the enzyme is expressed in fmol/min.

A.4 Measurement of Contractility

The myocytes are transferred into a chamber at 37° C., continuously perfused and positioned on the stage of an inverted microscope. The chamber is perfused with a physiological buffer containing (in mM): NaCl-140; KCl 5.4; $CaCl_2$ 1; $MgCl_2$ 0.8; HEPES 10 and glucose 5.6 (pH=7.4; 290 mOsmol/kg$H_2O$).

Contraction of the myocytes is induced once a second (1 Hz) with platinum field electrodes placed in the chamber and connected to a simulator. The images are captured continuously with a ×20 objective and transmitted to a CCD camera at a rate of 240 samples/s. The images of the CCD camera are projected on a video screen.

The myocytes were selected for the study according to the following criterion: a rod-like aspect with very apparent striations and no intracellular vacuola, no spontaneous contraction when they are stimulated with 1 mM $Ca^{2+}$, and with constant rest length and contraction amplitude. The length of the sarcomers was measured by a video image analysis program and the data were captured at a rate of 240 samples/s. The camera images are converted into sarcomer length measurements. The contraction percentage is calculated from these data on the length of the sarcoma.

A.5 Data Analysis

All the data are expressed as mean±standard deviation. Comparisons of data between the different groups were carried out by ANOVA followed by a Student test with a significant difference set to $p<0.05$.

Experimental Procedure

Apoptosis is induced in isolated cardiomyocytes by exposing them for 3 to 8 hrs to 1 µM of doxorubicin added in an isotonic solution containing (in mM) NaCl 110, KCl 5.4, $Na_2PO_4$ 0.33, $NaHCO_3$ 25, Glucose 5, $MgCl_2$ 0.8, $CaCl_2$ 1, pH adjusted to 7.4. Annexin V marking was carried out 3 hrs after the beginning of exposure to doxorubicin since this phenomenon appears very early in the apoptotic cascade. Caspase-3 activity measurements were conducted 8 hrs after exposure to doxorubicin since this phenomenon takes place later in the apoptosis phenomenon. The contractility of cardiomyocytes was measured every hour during the 8 hrs of exposure to doxorubicin. After all the treatments, the cells were compared with control cardiomyocytes not exposed to doxorubicin.

The cardiomyocytes were pretreated with the cholest-4-en-3-one oxime compound for 15 min before exposure to doxorubicin. Three concentrations of this compound were tested during this study: 0.3 µM, 1 µM and 3 µM.

Results

The mean length of the sarcomers of the cells used in this study was not significantly different among the groups.

Effect of Doxorubicin on the Contractility of Myocytes and on Apoptosis

Exposure to doxorubicin resulted in a reduction over time of the shortening of the sarcomer. The shortening of the doxorubicin peak was similar to that of the control for the first three hours and it then became significantly reduced after 4 hours of exposure (−53.20±7.70% versus −19.49±2.06% relatively to the base line of doxorubicin and of the control, $p<0.05$, n=5, respectively).

Treatment with 1 µM of doxorubicin induced apoptosis with a significant increase in annexin V marking and caspase-3 activity.

Effect of cholest-4-en-3-one Oxime on the Dysfunction at the Level of Contractility Induced by Doxorubicin and Apoptosis.

Treatment with 1 µM of doxorubicin resulted in a significant reduction in the shortening of the peak of ventricular cardiomyocytes, which is abolished in the presence of cholest-4-en-3-one oxime (0.3, 1 and 3 µM). Indeed, after 4 hrs of exposure, the shortening of the peak under doxorubicin (−53.20±7.70%) remains significantly reduced with the compound at 0.3 µM (−25.35±0.18%), at 1 µM (−15.66±5.72%) and at 3 µM (−13.95±3.17%) relatively to the base line.

Further, annexin V marking and caspase-3 activity increases due to doxorubicin were blocked by cholest-4-en-3-one oxime at 0.3, 1 and 3 µM.

Apoptosis evaluated as a change in % of annexin V marking, 3 hrs after doxorubicin gives the following results: control: 100%; doxorubicin: 291% 32; doxorubicin+0.3 µM cholest-4-en-3-one oxime: 130% 12.43; doxorubicin+1 µM cholest-4-en-3-one oxime: 121% 4.74; doxorubicin+3 µM cholest-4-en-3-one: 115.5% 16.35. The results concerning the measurements of caspase-3 activity are the following: control: 18±9 fmol/min; doxorubicin: 120±15 fmol/min; doxorubicin+0.3 µM cholest-4-en-3-one oxime: 33±9 fmol/min; doxorubicin+1 µM cholest-4-en-3-one oxime: 18±8 fmol/min; doxorubicin+3 µM cholest-4-en-3-one oxime: 11±4 fmol/min.

Comments and Conclusions

The cholest-4-en-3-one oxime compound shows a cardioprotective effect on the contractility dysfunction induced by doxorubicin and on apoptosis on isolated rabbit cardiomyocytes. The molecule, when it is used at appropriate doses may actually protect against cardiotoxicity induced by doxorubicin which is known as the limiting factor in the treatment of cancer patients with this anthracyclin. Thus, the cholest-4-en-3-one oxime compound may be used for limiting cardiotoxicity of doxorubicin in these patients.

EXAMPLE 2

Effect cholest-4-en-3-one Oxime in an In Vivo Model of Acute Hepatotoxicity

Hepatocytes like many other cells bear the Fas/CD95 receptor on their cytoplasmic membrane. Stimulation of the Fas route induces cell death by activating a cascade of caspases.

An acute hepatic damage model may be induced by a single injection of the Jo2 anti-Fas antibody (Ogasawara et al., Nature, August 1993), producing severe hepatic damages and resembling viral, auto-immune or drug-induced hepatitis.

Alanine Aminotransferase (ALAT) also called Serum Glutamic Pyruvic Transaminase (SGPT) is an enzyme present in hepatocytes. Its activity significantly increases in plasma after hepatic lysis and is therefore a good marker for evaluating hepatic damage.

The conducted experimentation consisted in intoxicating animals with Jo2 followed by an assay of ALATs and of testing the cholest-4-en-3-one oxime capability of protecting hepatocytes.

Materials and Methods

Animals

Male CD1 adult mice from the breeder "Elevage Janvier", (Le Genest-Saint-Isle, France) were used. The animals were identified individually and had free access to water and food.

The installations are maintained at a controlled light cycle (7:00 am-7:00 pm), and at temperatures of 20±2° C. with 50±20% humidity.

Preparation of the Jo2 Antibody

The stock solution of monoclonal hamster anti-mouse CD95 (Fas) antibody called Jo2, from Pharmingen (BD Biosciences, ref. 554254 batch 66081) is at a concentration of 1 mg/mL in water. The dilutions used are produced in 0.9% sodium chloride in water.

Preparation of the Compound to be Tested

The desired amount of cholest-4-en-3-one oxime is weighed and milled into a fine powder, and then suspended (60 mg/ml) in maize oil. The compound is administered orally (by force-feeding) at a concentration of 5 ml/kg.

Procedure

A pre-treatment with cholest-4-en-3-one oxime is carried out at a dose of 300 mg/kg per oral administration 4 hrs before administering the Jo2 antibody. The Jo2 antibody is administered by intra-peritoneal injection at a dose of 125 µg/kg in a volume of 5 mL/kg of body weight.

A control is obtained with animals receiving a pre-treatment by oral administration 4 hrs before administering the antibody with an identical volume of maize oil having been used for preparing the compound to be tested, without the compound.

Assaying ALATs

Blood from anesthetized mice is sampled 24 hrs after administering Jo2. Assaying ALATs is carried out by using a kit (Roche Diagnostics) with a spectrophotometer (Hitachi Modular), according to the method standardized by IFCC (International federation of Chemical Chemistry).

Results and Conclusions

Intra-peritoneal administration of Jo2 at 125 µg/kg induced the death of 3 mice among the 19 in the control group within 24 hrs following the injection.

ALAT activity is significantly reduced by the tested compound at 300 mg/kg.

TABLE 1

ALAT activity measured 24 hrs after administration of Jo2

| Treatment | ALAT activity (U/L) Mean +/− SEM (n) |
|---|---|
| Control | 2,586 ± 474 (16) |
| cholest-4-en-3-one oxime (300 mg/kg) | 1,136 ± 175 (20) ** |

** p = 0.0037, t-test carried out relatively to the control group

With cholest-4-en-3-one oxime administered at 300 mg/kg, 4 hrs before the Jo2 antibody, it was possible:
- to prevent the death of mice receiving the Jo2 antibody within 24 hrs following the injection;
- to limit cell death induced by a sublethal dose of antibody; the ALAT activity, biomarker of hepatic cytolysis in plasma, is significantly lower in mice treated with cholest-4-en-3-one oxime than in non-treated control mice.

Conclusions

With the acute hepatotoxicity model induced in mice by an anti-Fas (Jo2) antibody, hepatoprotective properties of cholest-4-en-3-one oxime may be demonstrated.

With these remarkable effects, compounds of formula I may be contemplated for a use in the preparation of a generally cytoprotective drug.

Toxicological Study

Administration in mice, in particular of cholest-4-en-3-one oxime, via oral, sub-cutaneous, intra-peritoneal and intravenous routes, at doses ranging up to 300 mg/kg/day, by means of a treatment with daily administration, which may extend for as far as 28 days, did not show any significant toxicity.

In monkeys, oral administration of increasing daily doses up to 1,500 mg/kg over a period of 10 days did not reveal any toxicity.

The invention claimed is:

1. A method for decreasing the risk of acquiring a cardiovascular disease in a cancer patient receiving doxorubicin, comprising administering to the patient a composition comprising cholest-4-en-3-one oxime or one of its addition salts with pharmaceutically acceptable acids.

2. The method according to claim 1, wherein the cardiovascular disease is a cardiovascular disease associated with mitochondria.

3. The method of claim 1, which reduces cell death in cardiac cells from necrosis and/or pathological apoptosis and/or necroptosis.

* * * * *